United States Patent
Punzmann et al.

(10) Patent No.: US 6,716,640 B2
(45) Date of Patent: Apr. 6, 2004

(54) STABILIZATION AND AMPLIFICATION OF ELECTROCHEMILUMINESCENCE SIGNALS

(75) Inventors: Gabriele Punzmann, Munich (DE); Martin Egger, Benried (DE); Hans-Peter Josel, Weilheim (DE)

(73) Assignee: Roche Diagnostics GmbH, Mannheim (DE)

( * ) Notice: Subject to any disclaimer, the term of this patent is extended or adjusted under 35 U.S.C. 154(b) by 433 days.

(21) Appl. No.: 09/853,244

(22) Filed: May 11, 2001

(65) Prior Publication Data

US 2001/0036673 A1 Nov. 1, 2001

Related U.S. Application Data

(62) Division of application No. 09/267,299, filed on Mar. 15, 1999, now Pat. No. 6,432,722.

(30) Foreign Application Priority Data

Mar. 17, 1998 (DE) .......................................... 198 11 582

(51) Int. Cl.[7] ............................................. G01N 33/558
(52) U.S. Cl. ............................ 436/514; 435/6; 435/7.1; 435/7.2; 436/84; 436/92; 436/172; 436/518; 436/546; 436/547; 436/548; 436/536; 436/537; 436/501; 436/517; 436/524; 436/538; 436/541; 436/544; 436/800; 436/805
(58) Field of Search ............................. 435/6, 7.1, 7.2; 436/172, 518, 84, 92, 514, 546, 547, 548, 536, 537, 501, 517, 524, 544, 538, 541, 800, 805; 556/136

(56) References Cited

U.S. PATENT DOCUMENTS

| 4,745,076 A | | 5/1988 | M+e,uml +ee uller et al. .. 436/537 |
| 5,310,687 A | | 5/1994 | Bard et al. ................... 436/518 |
| 6,066,448 A | * | 5/2000 | Wohlstadter et al. .......... 435/6 |

FOREIGN PATENT DOCUMENTS

| EP | 0178450 B1 | 4/1986 | ......... G01N/33/533 |
| EP | 0580979A2 A3 | 2/1994 | .......... G01N/33/52 |
| WO | WO 89/10551 | 11/1989 | .......... G01N/21/62 |
| WO | WO 90/05296 | 5/1990 | .......... G01N/21/66 |
| WO | WO 90/11511 | 10/1990 | .......... G01N/21/76 |
| WO | WO 96/03409 | 2/1996 | ........... C07F/15/00 |
| WO | WO 96/03410 | 2/1996 | ........... C07F/15/00 |

OTHER PUBLICATIONS

Blackburn, Gary F. " Electrochemiluminescence Detection for Development of Immunoassays and DNA Probe Assays for Clinical Diagnostics", Clinical Chemistry, Vol, 37, No. 9, 1991, 1534–1539.

Leland Jonathan K et al, " Electrogenerated Chemiluminescence: An Oxidative–Reduction Type ECL Reaction Sequence Using Tripropyl Amine", J. Electrochem Soc., vol. 137, No. 10, Oct. 1990, (5pgs).

* cited by examiner

Primary Examiner—Christopher L. Chin
(74) Attorney, Agent, or Firm—Marilyn L. Amick; Roche Diagnostics Corporation

(57) ABSTRACT

The invention concerns the stabilization and amplification of electrochemiluminescence signals in detection methods.

15 Claims, 3 Drawing Sheets

STABILIZATION AND AMPLIFICATION OF ELECTROCHEMILUMINESCENCE SIGNALS

Figure 1:
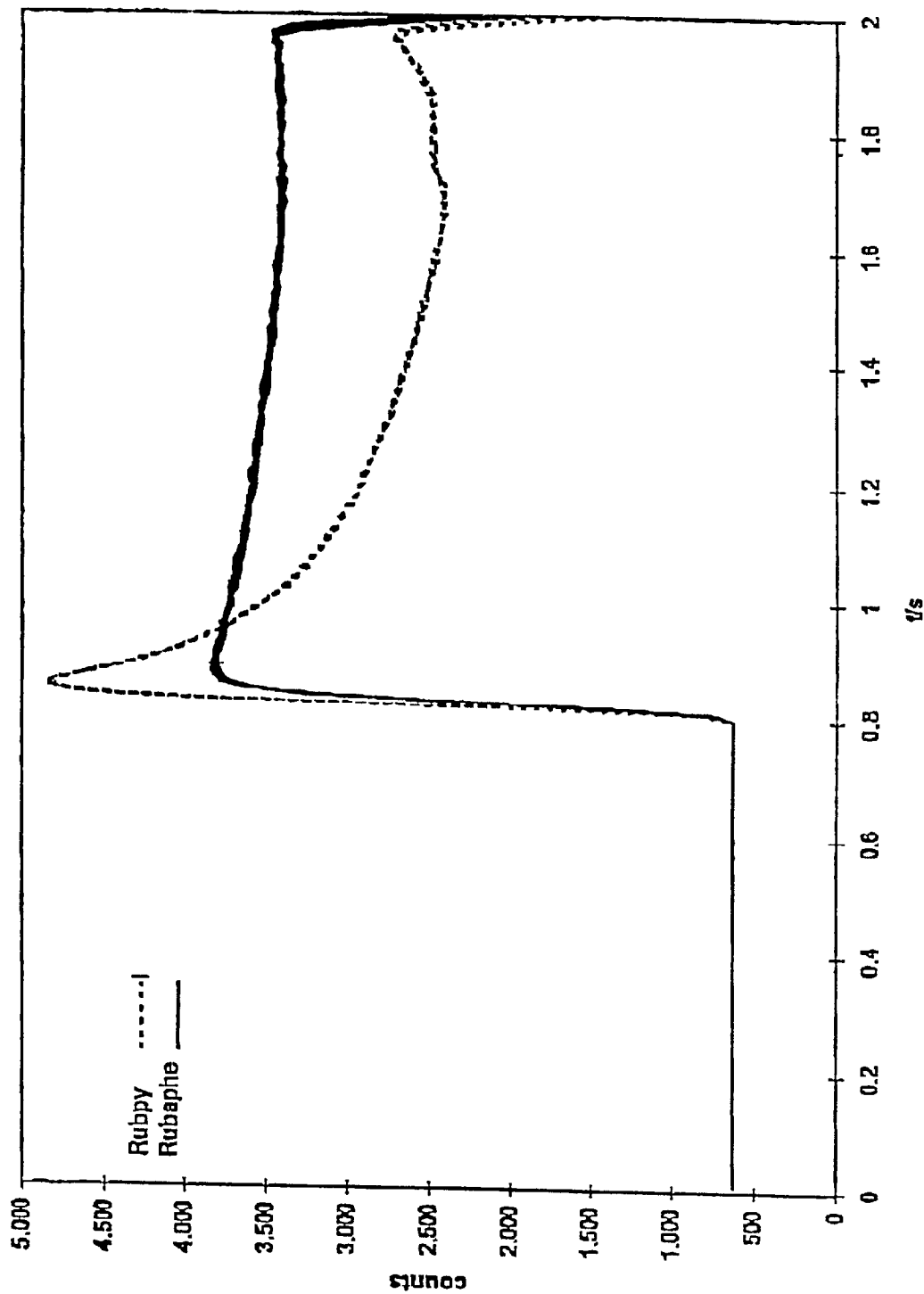

This application is a divisional application of U.S. Ser. No. 09/267,299 filed Mar. 15, 1999, now U.S. Pat. No. 6,432,722 issued Aug. 13, 2002.

DESCRIPTION

The invention concerns the stabilization and amplification of electrochemiluminescence signals in detection methods.

Luminescent metal complexes are known from the prior art. EP-A-0 178 450 discloses ruthenium complexes which are coupled to an immunologically active material where the ruthenium complexes contain three identical or different bicyclic or polycyclic ligands containing at least two nitrogen-containing heterocycles and at least one of these ligands is substituted with at least one group which renders it water-soluble such as —$SO_3H$ or —COOH and at least one of these ligands is substituted directly or via a spacer group with at least one reactive group such as —COOH and the ligands are bound to the ruthenium via nitrogen atoms.

In addition the use of metal complexes as labelling reagents for an electrochemiluminescence detection method is also known (cf. e.g. EP-A-0 580 979, WO 87/06706, U.S. Pat. No. 5,238,108 or U.S. Pat. No. 5,310,687). Such an electrochemiluminescence detection method is based on transfer of the central atom of the metal complex e.g. ruthenium into an excited MLCT triplet state by electron transfer in a suitable measuring device. From this excited state it can relax into the basic state by means of a forbidden triplet-singlet transition with emission of a photon (ef. e.g. WO/90 05296, Leland and Powell, J.Electrochem.Soc. 137 (1990), 3127–3131; Blackburn et al., Clin.Chem. 37 (1991), 1534–1539).

A disadvantage of this method is that the maximum obtainable level of the measurement signal is very limited due to a pronounced decrease of the signal intensity during the measuring phase. With the hitherto conventional procedure and the previous commercially used metal complexes, in particular ruthenium-(bipyridyl)$_3$ complexes this signal decrease already occurs after a measuring period of 100 ms and increases with the signal strength. This behaviour is not understandable on the basis of previous publications on the reaction mechanism, This decrease in the signal considerably limits the duration of the measurement and evaluation interval i.e. in practice to a maximum of 400 ms. In all previous cases this has led to a significantly reduced light yield which in turn results in a reduction of test sensitivity and test dynamics. Hence in practice it is only possible to use measurement and evaluation intervals of 400 ms at most without having problems with unspecific signals. Moreover imprecision and signal instabilities often occur in the decaying portion of the signal curve which lead to further inaccuracies.

New metal complexes with hydrophilic substituents or/and charge carriers on the linker are described in WO 96/03409 and WO 96/03410. Use of these complexes reduces an undesired adsorption which improves the stability and recovery in the detection method. Furthermore an increased quantum yield is described. However, no information is given about a possible extension of the maximum measurement interval in electrochemiluminescence measurements.

It was surprisingly found that the use of hydrophilic or/and charged metal complexes, for example according to EP-A-0 178 450, WO 96/03409 or WO 96/03410 results in considerable improvements in electrochemiluminescence detection since the signal decrease known for non-hydrophilic ruthenium-(bipyridine)$_3$ complexes does not occur. Surprisingly the signal maintains its maximum value essentially over the entire duration of the measurement interval. This leads to a signal amplification or/and to an increase in the duration of the maximum possible measurement interval. This improvement is preferably achieved under method conditions in which a negative potential is applied before the measurement to the measuring electrode in the presence of the electrochemiluminescence cosubstrate.

Hence one subject matter of the invention is a method for the detection of an analyte in a sample by electrochemiluminescence measurement comprising the steps:

(a) providing an electrochemiluminescence device comprising a measuring electrode, (b) bringing a conditioning liquid which contains an electrochemiluminescence cosubstrate into contact with the electrode (c) adjusting conditions at the electrode which lead to the formation of an activated molecule of the layer containing the electrochemiluminescence cosubstrate on or/and in the boundary region of the electrode e.g. by applying a negative potential to the electrode, (d) bringing the sample which contains a metal complex which contains at least one charge carrier or/and at least one hydrophilic group as an electrochemiluminescence marker group and an electrochemiluminescence cosubstrate into contact with the electrode, (e) applying a potential to the electrode which enables an electrochemiluminescence reaction to proceed and measuring the electrochemiluminescence and (f) correlating the measured luminescence with the presence or amount of the analyte in the sample.

The method according to the invention enables an at least two-fold to 5-fold higher measurement signal to be obtained due to the absence of a signal decrease compared to a conventional non-hydrophilic ruthenium-(bipyridyl)$_3$ marker group. This higher signal strength enables the use of cheaper semiconductor detectors instead of the previously used photomultiplyer tubes. Furthermore under suitable measurement conditions, i.e. maintaining an adequate positive potential for the luminescence reaction and at the same time maintaining an adequate supply of electrochemiluminescence cosubstrate, it is possible to generate a light quantity that remains constant per unit of time over any desired time interval. This enables a much larger quantity of light to be collected and achieves higher test sensitivities.

Additional advantages of the metal complexes used according to the invention are that less quenching by oxygen occurs and that there is less test interference for example by unspecific adsorption to test components or/and the electrode.

The electrochemiluminescence measuring device provided in step (a) of the method according to the invention can be a known device of the prior art (cf. for example N. R. Hoyle: The Application of electrochemiluminescence to Immunoassay-based Analyte Measurement, in: Bioluminescence and Chemiluminescence; Proceedings of the 8th International Symposium on Bioluminescence and Chemiluminescence, Cambridge, September 1994, A. K. Campbell et al. (publ.) John Wiley & Sons; WO 89/10551; WO 90/11511). The device preferably comprises a measuring chamber which holds the measuring electrode, means for supplying and removing liquids to and from the measuring chamber and means for detecting the electrochemiluminescence generated in the measuring chamber. In addition the device preferably contains magnetic means for immobilizing magnetic particles in the sample liquid on the measuring electrode.

Step (b) of the method comprises contacting the electrode with a conditioning liquid which contains an electrochemiluminescence cosubstrate which is effective as an oxidizing or reducing agent for the metal complex e.g. an amine or a persulfate. Tertiary amines such as trialkylamines are preferably used in which the alkyl residues each independently contain 1–4 C atoms. Tripropylamine is particularly preferred. The concentration of the cosubstrate in the conditioning liquid can be varied over wide ranges, it is preferably at least 1 mM, particularly preferably 10 to 500 mM and most preferably 100 to 300 mM. The conditioning liquid can additionally contain a suitable electrochemically inert buffer e.g. a phosphate buffer etc. and a detergent e.g. Thesit.

According to step (c) conditions are set on the electrode under which an attachment of activated and, in particular, reduced molecules of the cosubstrate occurs. The attachment can occur as an adsorption and also by formation of a boundary layer containing the cosubstrate molecules in the immediate vicinity of the electrode surface. For this purpose a negative potential is preferably applied to the electrode, preferably in the presence of the conditioning liquid. The level of the negative potential is preferably at least –0.3 V, for example –1.2 to –1.0 V. The negative potential is preferably applied for a duration of 0.2 to 20 s particularly preferably ca. 0.5 s.

Step (d) of the method according to the invention comprises contacting the sample with the measuring electrode. The sample is preferably a biological sample and is present in a liquid form. It can be derived from human, animal or plant tissues, body fluids, prokaryotic or eukaryotic cell cultures etc. The detection reagents required to determine the respective analyte are added to this sample. These detection reagents contain an electrochemiluminescent metal complex as defined in the following as a marker group which is preferably coupled to a biological substance e.g. biotin, nucleic acids, e.g. oligonucleotides, DNA or RNA, nucleic acid analogues such as peptidic nucleic acids, antibodies or antibody fragments, polypeptide antigens i.e. immunologically reactive polypeptides or haptens, i.e. organic molecules with a molecular weight of 150 to 2000 and optionally additional detection reagents as known to a person skilled in the art. The sample additionally contains an electrochemiluminescence cosubstrate as defined above.

The method according to the invention can be carried out as a homogeneous assay i.e. the electrochemiluminescence is measured in the liquid phase. However, a heterogeneous test is preferably carried out in which the electrochemiluminescent label is immobilized on a solid phase e.g. a particulate solid phase such as magnetic microbeads e.g. streptavidin-coated microbeads or on colloidal particles. When a heterogeneous test is carried out, the method according to the invention includes so-called capture and wash steps in which the solid phase is immobilized on the electrode and the other sample components are separated.

In order to measure the electrochemiluminescence, a potential is applied to the electrode according to step (e) which enables an electrochemiluminescence reaction to occur, i.e. an oxidative potential for the electrochemiluminescent metal complexes and the cosubstrates, and the electrochemiluminescence is determined. The oxidative electrode potential is preferably at least +1.2 V (relative to an Ag/AgCl reference electrode). Measuring potentials of at least +1.4 V e.g. between +1.4 V and +2.4 V are particularly preferred especially in the case of hydrophilic or/and charged ruthenium-bathophenanthroline complexes. The duration of the measurement interval can be considerably increased compared to the previous standard measurement period due to the non-occurrence of a signal decrease. The measurement interval is preferably at least 0.5 s particularly preferably at least 1 s and most preferably at least 2 s. In this connection it is preferable to apply an oxidative potential which is adequate to maintain the luminescence reaction during the entire duration of the measurement interval. It is particularly preferable to apply an essentially constant oxidative potential to the electrode during the entire measurement period.

Step (f) of the method according to the invention comprises correlating the measured electro-chemiluminescence with the presence or the amount of the analyte to be determined in the sample, This enables a qualitative or/and quantitative determination of analytes by standard methods that are known to a person skilled in the art.

An essential feature of the method according to the invention is the use of electrochemiluminescent metal complexes which contain a ligand together with a charge carrier or/and at least one hydrophilic group. A metal complex is preferably used as the marker group which contains a structure of the general formula (I):

in which

M is a divalent or trivalent metal cation selected from rare earth or transition metal cations, $L_1$, $L_2$ and $L_3$ are the same or different and denote ligands containing at least two nitrogen-containing heterocycles in which $L_1$, $L_2$ and $L_3$ are bound to the metal cation via nitrogen atoms, Y denotes a linker bound to the ligand by means of which the complex for example (a) is coupled to a biological substance or (b) can be coupled to a biological substance, m is an integer from 1 to 10, preferably from 1 to 4 and particularly preferably of 1, n is an integer from 1 to 6, preferably from 1 to 3 and particularly preferably of 1, and at least one hydrophilic group or/and a charge carrier is present in the complex.

The metal cation in this complex is preferably ruthenium, osmium, rhenium, iridium, rhodium, platinum, indium, palladium, molybdenum, technetium, copper, chromium, tungsten, yttrium or lutetium. Ruthenium, iridium, rhenium, chromium and osmium are particularly preferred. Ruthenium is most preferred. The complex can optionally contain counterions, e.g. anions, for charge equalization.

The ligands $L_1$, $L_2$ and $L_3$ are preferably ligands with at least 2 nitrogen-containing heterocycles. Aromatic heterocycles such as e.g. bipyridyl, bipyrazyl, terpyridyl and phenanthronyl are preferred. The ligands are particularly preferably selected from bipyridine and phenanthroline ring systems. The ligands most preferably contain bathophenanthroline ring systems.

The hydrophilic groups or/and the charge carriers in the metal complexes according to the invention are preferably covalently bound e.g. to the linker or to another substituent of the ligands $L_1$, $L_2$ or $L_3$. The term charge carrier denotes, in the sense of the present invention, a group which is mainly present in an ionic form at a pH value in the range of 6 to 8. The complex preferably contains up to 10, especially preferably 2 to 8 such charge carriers.

The complex particularly preferably contains at least one negative charge carrier. Examples of suitable negative charge carriers are phosphate, phosphonate, sulfonate and carboxylate groups of which sulfonate and carboxylate groups are most preferred.

Examples of positive charge carriers are amino and monosubstituted or polysubstituted amino groups such as mono, di or trialkylamino groups in which alkyl denotes a straight-chain or branched alkyl residue of 1–6 C atoms or a cyclic alkyl residue of 3–6 C atoms.

The linker between the ligand and the biological substance preferably has a chain length of 4 to 40 atoms and can be an alkylene chain modified by the incorporation of heteroatoms e.g. amide groups.

A linker which contains free charge carriers can for example be composed partially of aminocarboxylic acid units which are linked together by means of peptide bonds. In this case the charge carriers can be derived from free amino or/and carboxylate groups of polyfunctional aminocarboxylic acids which contain at least three charged groups (amino plus carboxylate) so that, after incorporation into the linker and the concomitant reaction of two of the charged groups, at least one free charge carrier is still present.

The free charge carriers can also be derived from substituents of the ligands which are not a component of the linker. These charge carriers can be bound directly or via a spacer group to the heterocyclic ring. If present, the spacer has a chain length of preferably 1–8 atoms and can be an alkylene chain modified by incorporation of heteroatoms e.g. amide groups.

In addition complexes are suitable for the method according to the invention which contain a hydrophilic group. Examples of suitable hydrophilic groups are $C_2$–$C_3$ alkyleneoxy units, $C_2$–$C_3$ alkylenethio units and polyhydroxy units.

The polyhydroxy units are preferably selected from the group of formulae (IIa) or (IIb):

   —NR—W   (IIa)

   —O—W—   (IIb)

in which

W denotes an organic residue containing at least 2 hydroxy groups and R denotes hydrogen or $C_1$–$C_5$ alkyl, preferably hydrogen or $C_1$ to $C_3$ alkyl.

The organic residue W preferably contains 2 to 6 and particularly preferably 2 to 4 hydroxy groups. In addition W should advantageously contain 2 to 10 and in particular 3 to 6 carbon atoms. Specific examples of suitable polyhydroxy units are residues of polyalcohols such as glycerol or aminopolyalcohols. A preferred amino alcohol is Tris(2-amino-2-hydroxymethyl)-1,3-propanetriol). The polyalcohols and aminopolyalcohols are preferably coupled to the metal complex in the form of esters and amides.

The $C_2$–$C_3$ alkyleneoxy and $C_2$–$C_3$ alkylenethio units of the metal complex according to the invention are preferably $C_2$ units and in particular ethyleneoxy units. The complex preferably contains 1 to 30 and preferably 2 to 20 alkyleneoxy or alkylenethio units per metal cation. The alkyleneoxy or alkylenethio units can optionally be linked to one another via a bridgehead. On the other hand it is also possible to link several complex units together via such a bridgehead to form semi-cage or cage structures.

Specific examples of suitable hydrophilic or/and charged metal complexes are given in EP-A-0 178 540, WO 96/03409 and WO 96/03410. Such metal complexes can be synthesized by known methods for example by reacting a metal salt e.g. a metal halogenide and optionally subsequently substituting the halogenide ion by hexafluorophosphate, trifluoroacetate or tetra-fluoroborate groups. Such methods are known. For the method according to the invention the metal complex is usually used in the form of conjugates with a biological substance in which case at least one metal complex is coupled to the biological substance. Examples of suitable biological substances are cells, viruses, subcellular particles, proteins, lipoproteins, glycoproteins, peptides, polypeptides, nucleic acids, oligosaccharides, polysaccharides, lipopolysaccharides, cellular metabolites, haptens, hormones, pharmacological agents, alkaloids steroids vitamins, amino acids and sugars.

The metal complex is preferably coupled to the biological substance by means of a reactive or activatable functional group on the metal complex e.g. a carboxylic acid halogenide, a carboxylic acid anhydride or an active ester such as an N-hydroxysuccinimide ester or a maleimide which can covalently couple to a functional group of the biological substance. If the functional group is a carboxylic acid anhydride, carboxylic acid halogenide or active ester, it is possible, for example, to couple to free amino groups of the biological substance. If the functional group is a maleimide residue, it can be coupled to free SH groups of the biological substance. An activation of functional groups of the biological substance can also be achieved in a similar manner which can for example be subsequently reacted with a free carboxylic acid, amino or thiol group of the metal complex.

Previous experimental results show that the metal complexes exhibit the improved signal properties i.e. an essentially constant signal over the entire measurement period as a free complex and also when coupled to a biological substance e.g. an antibody (for a homogeneous assay) or when immobilized on a solid phase e.g. paramagnetic microbeads via a high affinity binding e.g. an immunological or a biotin-streptavidin binding. Unexpected additional advantageous properties of the method according to the invention are that the unspecific binding of a conjugate composed of a biological substance and a metal complex to the solid phase e.g. microbeads is much less than with previously used metal complexes and method conditions. Improvements were also found with regard to unspecific binding to the electrode surface. Furthermore the conjugate composed of a metal complex according to the invention and a biological substance, for example in a free form can exhibit higher signal amplitudes in a homogeneous test variant than a previously used conjugate at the same concentration.

Yet a further subject matter of the present invention is a method for the detection of an analyte in a sample by electrochemiluminescence in which a metal complex which contains at least one charge carrier or/and at least one hydrophilic group is used as the electrochemiluminescence marker group and the measurement is carried out for a period of at least 0.5 s, preferably of at least 1 s and particularly preferably of at least 2 s. Preferred features of this method are comprehensively elucidated above.

The present invention is additionally illustrated in more detail by the following examples and figures.

Figure 2:
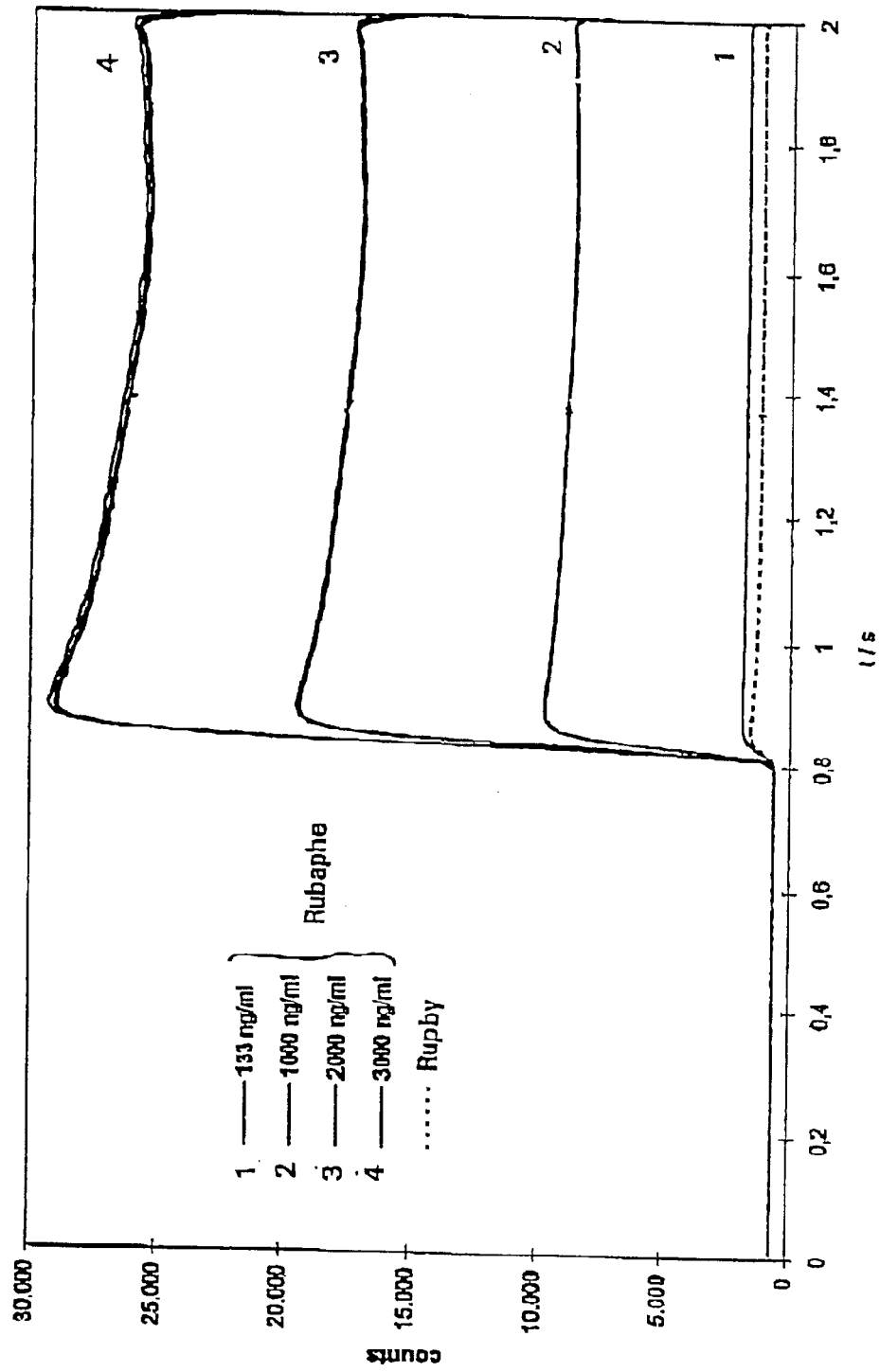
Figure 3:
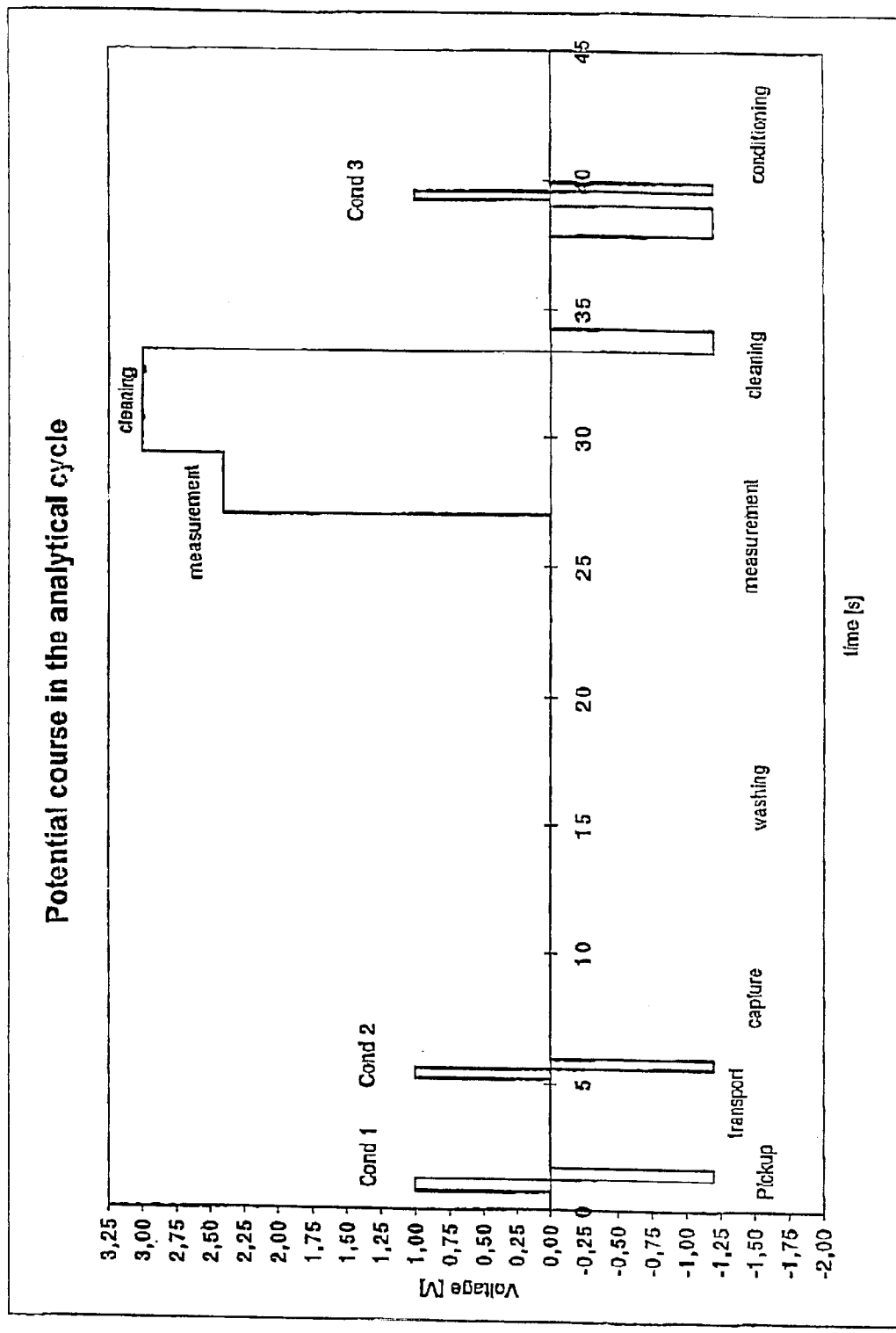

FIG. 1 shows a comparison of luminescence measurements using free Rubipy and Rubaphe complexes, FIG. 2 shows a comparison of luminescence measurements using Rubipy- and Rubaphe-antibody complexes and FIG. 3 shows a possible potential curve in an analytical cycle.

EXAMPLES

Example 1

Homogeneous Test Procedure

The ruthenium(bipyridyl)$_3$ complex (Rubpy) and ruthenium-(bathophenanthroline(SO$_3$)$_2$)$_3$ complex (Rubaphe) were prepared according to EP-A-0 178 450 or WO 96/03410. These complexes were coupled to polyclonal anti-T4 IgG antiserum from sheep by standard methods. The instrument used was an Elecsys 2010 series instrument The test procedure was carried out using an analytical cycle which essentially corresponds to the potential profile of the heterogeneous test described in example 2 except that microparticles and a bound-free separation were not used. Therefore instead of capturing the micro-particles on the electrode surface, a segment of solution containing marker molecules bounded by air bubbles had to be positioned over the electrode in the measurement chamber. Afterwards the luminescence was measured.

In a first test the metal complexes Rubpy and Rubaphe were each examined alone (at concentrations of 10 nM) or as antibody conjugates 1:15 (133 ng) in a homogeneous test procedure. The duration of the evaluation interval was 400 ms or 1.2 s. The results of these tests are summarized in Table 1.

TABLE 1

| Homogeneous test on an Elecsys 2010 series instrument | Signal yield with an evaluation interval of 400 ms (0.8–1.2 s) | Signal yield with an evaluation interval of 1.2 s (0.8–2.0 s) | Improvement factor standard versus longer evaluation interval |
|---|---|---|---|
| Rubpy (only label) | 115185 counts | 270027 counts | 2.3 |
| Rubaphe (only label) | 117212 counts | 338435 counts | 2.8 |
| improvement factor Rubaphe/Ruby | 1.02 | 1.3 | |
| Rubpy (antibody conjugate 1:15) | 29119 counts | 72326 counts | 2.4 |
| Rubaphe (antibody conjugate) | 46647 counts | 136719 counts | 2.9 |
| improvement factor Rubaphe/Rubpy | 1.6 | 1.9 | |

In the case of the homogeneous test procedure a signal increase was found when using Rubaphe compared to Rubpy. Rubaphe resulted in a significantly better signal than Rubpy especially with a longer evaluation interval.

The graphic result of a measurement using the free complex in analytical buffer is shown in FIG. 1. It can be seen that Rubaphe has an essentially constant signal course over the entire duration of the signal whereas in the case of Rubpy there is already a considerable decrease in the signal after a few milliseconds.

FIG. 2 shows the result of a measurement using antibody-metal complex conjugates. Also in this case the superiority of Rubaphe compared to Rubipy can be seen.

Example 2

Heterogeneous Test Procedure Using Microparticles

A heterogeneous competitive test for progesterone 2 G was carried out. For this 75 µl Rubipy or Rubaphe progesterone conjugate (20 ng/ml) and 10 µl streptavidin-coated microparticles were added to 85 µl of a biotinylated monoclonal anti-progesterone IgG antibody (60 ng/ml). The progesterone-ruthenium complex conjugates were prepared analogously to WO 96/03410 by coupling an activated metal complex (N-hydroxysuccinimide ester) to progesterone-3-CMO-aminodioxaoctane in DMF. The total incubation period for this step was 8.4 min. Then 30 µl of the sample to be tested was added and it was incubated for a further 8.4 min; then a luminescence measurement was carried out.

The course of an analytical cycle is shown in FIG. 3 on the basis of the potential profile. The conditioning steps named Cond 1, Cond 2 and Cond 3 and in particular Cond 2 with the reductive part contained therein (negative potential relative to the Ag/AgCl reference) are of major importance for conditioning the electrode and for a continuous signal with the tested metal complexes. The result for Rubpy and Rubaphe is shown in Table 2.

TABLE 2

| Calibrator | Concentration progesterone (ng/ml) | Rubaphe signals | Rubpy signals |
|---|---|---|---|
| Cal 1 | 0 | 160893 | 257102 |
| Cal 2 | 2 | 116140 | 193590 |
| Cal 3 | 5 | 78362 | 142102 |
| Cal 4 | 10 | 52570 | 101752 |
| Cal 5 | 20 | 43306 | 89240 |

TABLE 2-continued

| Calibrator | Concentration progesterone (ng/ml) | Rubaphe signals | Rubpy signals |
|---|---|---|---|
| Gal 6 | 70 | 33806 | 67518 |
| Cal 7 | 100 | 31446 | 62772 |

Rubpy results in a 60% higher maximum signal in the absence of progesterone. However, since the minimum signal (100 ng/ml progesterone) in the case of Rubpy is ca. 200% higher than Rubaphe, this results in at least 20% better signal dynamics (ratio of maximum signal strength to minimum signal strength) for Rubaphe.

What is claimed is:

1. A method for determining the presence or amount of an analyte in a sample by electrochemiluminescence measurement comprising the steps of:

a) providing an electrochemiluminescence device comprising a measuring electrode, b) bringing a conditioning liquid which contains an electrochemiluminescence cosubstrate into contact with the electrode, c) applying a negative potential to the electrode, thereby forming a layer containing activated molecules of the electrochemiluminescence cosubstrate on the electrode, d) bringing the sample and a detection reagent into contact with the electrode, the detection reagent comprising a marker group coupled to a substance immunologically reactive with the analyte, the marker group comprising a metal complex comprising a group selected from the group consisting of charge carriers and hydrophilic groups and generating a detectable signal upon reaction with the analyte, e) applying a potential to the electrode which enables an electrochemiluminescence reaction to proceed, f) measuring the signal during a measurement interval of at least 0.5 seconds, and g) correlating the measured signal with the presence or amount of the analyte in the sample.

2. The method of claim 1, wherein the metal complex has a structure of the general formula:

$$[M(L_1L_2L_3)]_n\text{—}Y_m$$

in which
M is a divalent or trivalent metal cation selected from rare earth or transition metal cations, $L_1$, $L_2$ and $L_3$ are the same or different and denote ligands containing at least two nitrogen-containing heterocycles in which $L_1$, $L_2$ and $L_3$ are bound to the metal cation via nitrogen atoms, Y denotes a linker bound to the ligand,
m is an integer from 1 to 10,
n is an integer from 1 to 6, and
at least one group selected from hydrophilic groups and charge carriers is present in the complex.

3. The method of claim 2, wherein the hydrophilic group or the charge carrier is bound to a linker or to a further substituent of the ligands $L_1$, $L_2$ and $L_3$.

4. The method of claim 1, wherein the metal complex is a ruthenium complex.

5. The method of claim 2, wherein the ligands $L_1$, $L_2$ and $L_3$ contain bipyridine or phenanthroline ring systems.

6. The method of claim 2 wherein the ligands contain bathophenanthroline ring systems.

7. The method of claim 1, wherein the charge carrier is a negative charge carrier selected from the group consisting of phosphate, phosphonate, sulfonate and carboxylate groups.

8. The method of claim 1, wherein the hydrophilic group is selected from the group consisting of $C_2$–$C_3$ alkyleneoxy units, $C_2$–$C_3$ alkylenethio units and polyhydroxy units.

9. The method of claim 1, wherein the electrochemiluminescence cosubstrate comprises a trialkylamine in which the alkyl residues each contain independently of one another 1–4 C atoms.

10. The method of claim 9, wherein the trialkylamine is tripropylamine.

11. The method of claim 1, wherein the potential applied in step (c) is −0.3 to −1.2 V (relative to an Ag/AgCl reference electrode).

12. The method of claim 1, wherein the potential applied in step (e) is applied during the entire measurement interval.

13. The method of claim 1, wherein the potential applied in step (e) is a positive electrode potential of at least +1.2 V (relative to an Ag/AgCl reference electrode).

14. The method of claim 1, wherein the method is carried out as a homogeneous test.

15. The method of claim 1, wherein the method is carried out as a heterogeneous test.

* * * * *